(12) United States Patent
Börner et al.

(10) Patent No.: US 8,841,075 B1
(45) Date of Patent: Sep. 23, 2014

(54) HOMOLOGOUS PAIRING CAPTURE ASSAY AND RELATED METHODS AND APPLICATIONS

(75) Inventors: G. Valentin Börner, Cleveland Heights, OH (US); Neeraj Joshi, Cleveland, OH (US)

(73) Assignee: Cleveland State University, Cleveland, OH (US)

(*) Notice: Subject to any disclaimer, the term of this patent is extended or adjusted under 35 U.S.C. 154(b) by 398 days.

(21) Appl. No.: 13/085,051

(22) Filed: Apr. 12, 2011

Related U.S. Application Data

(60) Provisional application No. 61/323,375, filed on Apr. 13, 2010.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
USPC .............................................. 435/6.12, 91.2
See application file for complete search history.

(56) References Cited

U.S. PATENT DOCUMENTS

| | | | |
|---|---|---|---|
| 2002/0169138 A1* | 11/2002 | Kunz et al. | 514/44 |
| 2006/0088850 A1 | 4/2006 | Tapscott et al. | |
| 2009/0062132 A1 | 3/2009 | Borner | |
| 2010/0130373 A1 | 5/2010 | Dekker et al. | |
| 2010/0273151 A1 | 10/2010 | Tapscott et al. | |

OTHER PUBLICATIONS

Knobler et al. Journal of Medical Virology, 1989, vol. 29, p. 33-37.*
Oppenheim. Nucleic Acids Research, 1981, vol. 9(24). p. 6805-6812.*
Job Dekker, Karsten Rippe, Martijn Dekker, Nancy Kleckner; "Capturing Chromosome Conformation"; Science; Feb. 15, 2001; pp. 1306-1311; vol. 295.
Bill Wickstead, Klaus Ersfeld, Keith Gull; The Small Chromosomes of *Trypanosoma brucei* Involved in Antigenic Variation Are Constructed Around Repetitive Palindromes; Genome Res. 2004, 14: 1014-1024; Cold Spring Harbor Laboratory Press; Manchester, UK.
Nikhil U. Nair, Huimin Zhao; Mutagenic inverted repeat assisted genome engineering (MIRAGE); Nucleic Acids Research, 2009, vol. 37, No. 1 e9; University of Illinois at Urbana-Champaign; Urbana, Ill, US.
Alison J. Rattray: A method for cloning and sequencing long palindromic DNA junctions; Nucleic Acids Research 2004, vol. 32, No. 19, e155; Oxford University Press; Frederick, MD, US.

* cited by examiner

*Primary Examiner* — Kenneth R. Horlick
*Assistant Examiner* — Joyce Tung
(74) *Attorney, Agent, or Firm* — Mark E. Bandy; Rankin, Hill & Clark LLP

(57) ABSTRACT

A Homologous Pairing Capture Assay is described which enables detection of coalignment between homologous DNA sequences. The assay involves ligating closely positioned homologous sequences to each other thereby generating head-to-head ligation products or inverted repeats. DNA fragments containing an inverted repeat are then converted into hairpin DNA molecules. The hairpin DNA molecules can then be readily separated from DNA molecules free of inverted repeats. Also described are various diagnostic applications and kits relating to the assay.

18 Claims, 7 Drawing Sheets

HOMOLOGOUS PAIRING CAPTURE ASSAY AND RELATED METHODS AND APPLICATIONS

CROSS REFERENCES TO RELATED APPLICATIONS

The present application claims priority upon U.S. provisional application Ser. No. 61/323,375 filed Apr. 13, 2010.

FIELD OF THE INVENTION

The present invention relates to the field of detection of specific DNA sequences in complex mixtures of DNA, within or outside of cells. The present invention also relates to the field of chromosome structure and genome stability. The present invention further relates to the field of genetic mapping.

SUMMARY OF THE INVENTION

Specifically, a method is described for identifying closely juxtaposed pairs of homologous DNA segments. Close juxtaposition between pairs of DNA segments indicates a high frequency of physical interactions. Physical interactions are typically captured by a crosslinking agent, and a higher frequency of physical interactions will result in a relative increase in crosslinking frequency compared to the crosslinking frequencies between pairs of DNA segments that do not physically interact. The exact distance detected as physical interaction is determined by the chemical or physical composition of the crosslinking agent. For example, crosslinking by formaldehyde plus ethylene glycolbis[succinimidyl succinate] generates crosslinks over a longer distance compared to formaldehyde alone. Homologous pairing typically comprises sequences preferably at least 20 bp, more preferably 20 bp to 100 bp, and most preferably more than 100 bp. However, homologous pairing can involve sequences less than 20 bp. Stable alignment of homologous sequences (herein referred to as "pairing") is a key determinant for alignment and recombination between homologous chromosomes during meiosis. Pairing also plays an important role in the repair of chromosome breaks and integration of DNA sequences via homologous recombination. Pairing is further implicit in most models of mitotic chromosome structure.

To detect pairing between homologous sequences, the present invention provides a Homologous Pairing Capture (HPC) assay that uses methods related to the chromosome confirmation capture (3C) assay (a method developed to detect interactions between non-homologous DNA sequences) and rapid intramolecular reannealing (a method that allows selective detection of inverted repeat sequences). Generally, in accordance with the invention, closely juxtaposed sequences are joined or ligated to each other, generating head-to-head ligation products. Such ligation products, when involving homologous sequences, are also known as inverted repeats. DNA fragments that contain an inverted repeat are subsequently converted into hairpin DNA molecules by denaturation followed by rapid intrastrand annealing while DNA molecules without inverted repeats are converted into single stranded DNA molecules which can be specifically eliminated, resulting in the specific enrichment of pairing-derived sequence elements.

In one aspect, the present invention provides a method for detecting pairing between homologous nucleic acid (DNA) sequences. The method comprises providing a system containing DNA species. The method also comprises forming inverted repeats from homologous pairing partners in a portion of the DNA species that include a homologous sequence that is spatially juxtaposed with another homologous sequence, whereby the DNA species not including juxtaposed homologous sequences are not converted into inverted repeats. The method additionally comprises forming hairpin DNA molecules from the inverted repeats. The method also comprises forming single stranded DNA molecules from the portion of the DNA species that do not contain inverted repeats. And, the method also comprises separating the single stranded DNA molecules from the hairpin DNA molecules, thereby enabling detection of pairing between homologous DNA sequences.

In another aspect, the present invention provides a kit for detecting pairing between homologous nucleic acid (DNA) sequences in DNA species. The kit comprises at least one crosslinking agent. Upon reacting the homologous DNA sequence with the crosslinking agent, stabilized pairing interactions are formed. The kit also comprises at least one agent for forming head-to-head ligation products from the stabilized pairing interactions. Head-to-head ligation products formed from closely juxtaposed pairs of homologous DNA sequences are inverted repeats. The kit also comprises at least one agent for forming hairpin molecules from inverted repeats. The kit may additionally comprise at least one single strand specific nuclease as well as BND cellulose for eliminating any single strand DNA species from the hairpin molecules. The kit may also comprise the buffer solutions for each step and prepacked columns containing materials such as BND cellulose.

As will be realized, the invention is capable of other and different embodiments and its several details are capable of modifications in various respects, all without departing from the invention. Accordingly, the drawings and description are to be regarded as illustrative and not restrictive.

BRIEF DESCRIPTION OF THE DRAWINGS

FIG. 3A depicts a restriction map. FIG. 3B illustrates intramolecular annealing. FIG. 3C illustrates S1 sensitive repeats in trans. And, FIG. 3D shows Southern blots with repeat specific probes in lanes 1-3 and 7-9, with relevant lanes from agarose gel shown in the left panels.

FIG. 8A depicts radial chromatin loops emanating from a scaffold of partially deproteinized chromosomes. FIG. 8B illustrates coiled chromosome scaffolds of opposite handedness revealed by condensin staining. FIG. 8C depicts a 3D model of FIG. 8B. FIG. 8D illustrates chromosomes carrying three consecutive GFP-IacI binding sites.

DETAILED DESCRIPTION OF THE EMBODIMENTS

Figure 1:
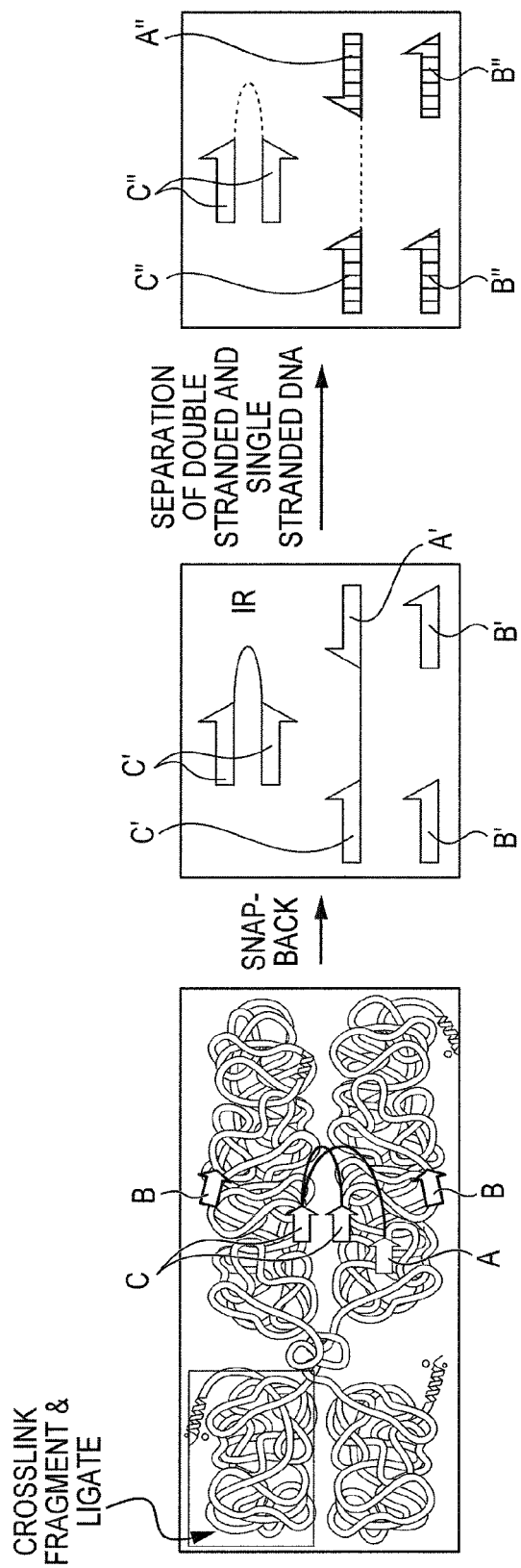
FIG. 1 is a schematic illustration of a preferred embodiment method in accordance with the present invention, referred to herein as a Homologous Pairing Capture (HPC) assay.

Identification of Paired Sequences Via a Homologous Pairing Capture (HPC) Assay DNA sequences involved in homologous pairing are difficult to identify due to limitations of current pairing assays. Assays for identifying interaction frequencies between non-homologous sequences, specifically the chromosome conformation capture (3C) assay, are not applicable to detection of pairing between homologous sequences since during the 3C procedure, inverted repeat sequences are generated which are refractory to PCR amplification. Cytological assays including fluorescent in situ hybridization (FISH) are only applicable to cellular structures such as chromosomes, but not to DNA molecules in solution, are limited to small sample sizes, and are susceptible to artifacts induced by extraction of chromosomes from cells.

The current invention provides an assay, referred to herein as Homologous Pairing Capture (HPC), to specifically enrich pairing sites in complex mixtures of DNA sequences. In this assay, paired homologous sequences are selectively preserved with concurrent elimination of other genomic sequences. Specifically, transient interactions between closely juxtaposed segments of homologous DNA segments are stabilized by exposing intact cells to a crosslinking agent to stabilize pairing interactions. Different crosslinking agents are used for different types of pairing interaction. For example, sequences that are paired in the presence of or depending upon proteins, are crosslinked via an agent that introduces covalent bonds between proteins, and between DNA and protein, for example formaldehyde. Sequences paired via a strand invasion events and involving single or double Holliday junctions are crosslinked via interstrand crosslinking agents, for example psoralen, or stabilized by extraction methods that prevent branch migration, for example by use of CTAB (hexadecyltrimethylammonium bromide). Importantly, crosslinks must be reversible.

Following stabilization of transient pairing interactions, these interactions are converted into specific ligation products by DNA fragmentation, followed by ligation of crosslink-connected sequence pairs. Ligation is preferably carried out at low DNA concentration to minimize ligation of DNA segments not connected via crosslink stabilized bridges.

Following ligation and denaturation of the DNA ligase, crosslinks are reversed, DNA is extracted, and the sample is heat-denatured and rapidly renatured. Denaturation and renaturation are preferably carried out under volume and buffer conditions that maximize annealing between homologous sequences but minimize annealing between non-homologous sequences. These objectives can be achieved for example, by varying the salt and formalin concentration in the denaturation/renaturation buffer. Head-to-head ligation products between homologous sequences generates Inverted repeats (IRs) which undergo intrastrand reannealing into double stranded DNA (periodically referred to herein as "dsDNA") hairpins when denatured and rapidly renatured (a process periodically referred to herein as "snapback"). Ligation products between non-allelic segments and unligated DNA fragments remain single stranded after snapback. Elimination of single stranded DNA (periodically referred to herein as "ssDNA") by a single strand specific nuclease, for example S1 or P1 nuclease, with concurrent preservation of DNA sequences involved in hairpin molecules results in specific enrichment of sequences engaged in homologous pairing. In addition, single stranded DNA can be separated from double stranded DNA by adsorption of the snapback treated sample to BND cellulose. In the preferred embodiment, a round of adsorption of ssDNA to BND cellulose is followed by a second round of denaturation and renaturation followed by S1 nuclease digest. Thus, the HPC assay specifically enriches for DNA segments engaged in homologous pairing.

FIG. 1 is an illustration of a preferred embodiment method in accordance with the invention, referred to herein as a Homologous Pairing Capture Assay. Arrows and half-arrows represent dsDNA and ssDNA, respectively. Corresponding letters, i.e. A, B, or C, indicate pairs of allelic/homologous sequences (B,C) or a single nonhomologous sequence (A), respectively. Head-to-head ligation products of pairs of homologous sequences generate inverted repeats (IR) which are converted to hairpins by intrastrand reannealing. dsDNA regions within hairpins are selectively resistant to S1 digest. Thus, head-to-head ligated homologous sequences such as CC comprise inverted repeats. Other species such as CA and B do not form inverted repeats. Double stranded sequences A, B, and C are subjected to snapback, i.e. denatured and rapidly renatured, to produce single stranded species A', B', and C'. Upon subjecting the various species to intrastrand reannealing, any inverted repeats such as CC are converted to hairpin molecule C'C'. Ligation products comprising non-allelic sequences such as species C'A' and unligated sequences such as B' are not converted to hairpin molecules and remain single stranded after snapback. Single stranded molecules are then separated from double stranded molecules. Preferably, single stranded molecules are eliminated by S1 nuclease digest, preceded by an optional adsorption to BND cellulose, resulting in retention of hairpins such as C"C" and elimination of single stranded molecules such as C"A" and B".

A side product of ligation at low concentration is circularized DNA which frequently forms due to intramolecular ligation. Circularized DNA molecules also frequently carry supercoils. Circular, supercoiled dsDNA is not easily converted into ssDNA by standard denaturation and renaturation due to plectonemic connections/intertwining of the two circular DNA molecules. Supercoiled, circular DNA molecules can however, be denatured when the DNA is treated prior to heat denaturation with a nicking enzyme or a type I (or type II) topoisomerase. Nicking prior to heat denaturation substantially reduces the abundance of circular, supercoiled DNA molecules resistant to ssDNA specific nuclease. Alternatively, circular/supercoiled DNA circles are separated from linear DNA by 2-dimensional agarose gel electrophoresis. The lower arc on an ethidium bromide stained 2D gel contains linear DNA molecule while the upper arc contains circular DNA molecules. Linear DNA molecules including unligated as well as allelic and non-allelic ligation products (corresponding to the lower arc) are cut out and eluted from the agarose gel and subjected to heat denaturation followed by rapid renaturation, adsorption to BND cellulose, a second round of snapback and S1 nuclease digestion.

Following elimination of single stranded DNA, i.e. derived from DNA segments unligated or ligated to non-homologous DNA sequences, the remaining DNA is amplified by a method that enriches for dsDNA, such as linker-mediated PCR. The relative abundance of sequences is determined in the HPC treated sample by competitive genome hybridization (CGH) or massively parallel sequencing approaches. Sequences from an HPC treated sample are compared to two control samples: In control 1, DNA ligation is carried out after DNA extraction without stabilization of in vivo juxtaposition. In control 2, the treatment required for intrastrand reannealing is omitted, but all other treatment steps are carried out as described for the HPC sample.

To summarize, an HPC treated sample is preferably treated by: crosslinking/stabilization of interactions, cell lysis, DNA fragmentation, ligation at low DNA concentration, reversal of crosslinking, DNA extraction, denaturation, followed by rapid renaturation, adsorption to a matrix that preferentially binds to ssDNA, another round of denaturation and renaturation and digestion of single stranded DNA, opening of hairpin DNA, amplification of preserved DNA, and sequence analysis. In control samples, (i) denaturation followed by rapid reannealing is omitted or (ii) pairing stabilization is omitted and DNA is ligated following its extraction, i.e. release from features that mediate pairing. If fragmentation of crosslinked DNA is carried out such that cleavage of the two DNA molecules occurs at two non-allelic positions, BND cellulose can not be used as a method to eliminate ssDNA due to the presence of an extended single stranded region in the hairpin region connecting the two homologous sequence segments. Increased specificity can be achieved by repeated rounds of snapback followed by adsorption to a matrix that preferentially binds to single stranded DNA. No additional rounds of snapback can be performed following nuclease digest if the nuclease cleaves the single stranded region of the hairpin.

More specifically, a preferred version of the HPC assay is as follows. Generally, a system containing DNA species is provided. Optionally, it may be preferred to stabilize transient pairing interactions. This can be performed by exposing the DNA species to one or more crosslinking agents to stabilize any pairing interactions. Inverted repeats are formed from the portion of the DNA species that are spatially juxtaposed with another homologous DNA sequence, whereby the DNA species not juxtaposed to homologous sequences are not converted into inverted repeats. Inverted repeats from homologous pairing partners are formed by generating head-to-head ligation products. Optionally, at this juncture, it may be preferred to subject any supercoiled, circular DNA in the DNA species to nicking. Alternately, it may be preferred to separate any supercoiled, circular DNA in the DNA species from linear ligation products by other means, for example 2D gel electrophoresis or BND cellulose chromatography. Hairpin DNA molecules are then formed from the inverted repeats. A preferred process for forming hairpin DNA molecules is by rapid intrastrand annealing. Single stranded DNA molecules that do not contain inverted repeats are then formed. In a subsequent operation, the single stranded DNA molecules are separated from the hairpin DNA molecules, thereby enabling detection of pairing between homologous DNA sequences. Separating the single stranded DNA molecules from the hairpin DNA molecules can be performed by adsorbing DNA molecules to a matrix that preferentially retains single stranded DNA, by eliminating single stranded DNA molecules by a single strand specific nuclease, or by a combination of both approaches. Optionally, after performing such separation of the single stranded DNA molecules from the hairpin DNA molecules, the remaining hairpin DNA molecules may be subjected to an amplifying operation. Each of these operations is described in greater detail herein.

System Containing DNA Species

One or more samples containing DNA species to be analyzed are obtained or otherwise provided. Strategies for this operation are well known in the art.

Stabilizing Transient Pairing Interactions

It may be preferred to stabilize any transient pairing interactions in the system containing the DNA species of interest. This can be performed by exposing or reacting the DNA species to one or more crosslinking agents to stabilize any pairing interactions. Crosslinking typically occurs in intact cells. Transient interactions between closely juxtaposed segments of homologous DNA segments can be stabilized by exposing intact cells to a crosslinking agent to stabilize pairing interactions. Different crosslinking agents are used for different types of pairing interaction. For example, sequences that are paired in the presence of, or depending upon proteins, are crosslinked via an agent that introduces covalent bonds between proteins, and between DNA and protein, for example formaldehyde. Additional examples of crosslinking agents for sequences paired in the presence of, or depending upon proteins, include but are not limited to dimethyl adipimidate, disuccinimidyl suberate; dithiobis succinimidyl propionate, ethylene glycolbis[succinimidyl succinate], and DNA intercalating agents linked to biotin-streptavidin. Sequences paired via strand invasion events and involving single or double Holliday junctions are crosslinked via interstrand crosslinking agents, for example psoralen. Additional non-limiting examples of interstrand crosslinking agents include difunctional alkylating agents. The invention also includes the use of stabilization methods to stabilize transient pairing interactions such as, but not limited to extraction methods that prevent branch migration, for example by reaction with CTAB (hexadecyltrimethylammonium bromide). Importantly, crosslinks must be reversible.

Forming Inverted Repeats

Inverted repeats are formed from the portion of the DNA species that are spatially juxtaposed with another homologous DNA sequence, whereby the DNA species not juxtaposed to homologous sequences are not converted into inverted repeats. Inverted repeats from homologous pairing partners are formed by generating head-to-head ligation products. Once stabilized, the transient pairing interactions are preferably converted into specific ligation products by DNA fragmentation, followed by ligation of crosslink-connected sequence pairs. DNA fragmentation can be performed by several methods. For example, DNA fragmentation can be performed by use of a restriction enzyme, sonication, adaptive focused acoustics (AFA), or enzymatic, sequence non-specific fragmentation (also known as Fragmentase), or combinations of these techniques. Ligation is preferably carried out at low DNA concentration to minimize ligation of DNA segments not connected via crosslink stabilized bridges. DNA concentrations typically are about 1 microg/ml.

Depending upon the particular technique used for forming head-to-head ligation products which thus includes inverted repeats if closely juxtaposed pairs of homologous DNA sequences are present, typical agents for forming head-to-head ligation products include but are not limited to T4 DNA ligase or *E. coli* DNA ligase.

Nicking

Optionally, at this juncture, it may be preferred to subject any supercoiled, circular DNA in the DNA species to nicking.

The term "nick" refers to a discontinuity in a double stranded DNA molecule where there is no phosphodiester bond between adjacent nucleotides of one strand typically through damage or enzyme action. Thus, the term "nicking" as used herein refers to the formation of such a discontinuity. Nicking can be performed by addition of a nicking sequence-specific endonuclease, a topoisomerase, or other agent such as mutant Vvn endonuclease.

Separating Supercoiled, Circular DNA from Linear Ligation Products

In certain applications, it may be preferred to separate any supercoiled, circular DNA in the DNA species from linear ligation products. A preferred method for performing such separation is by 2-dimensional gel electrophoresis. However, the present invention includes the use of other separation strategies.

Forming Hairpin Molecules from Inverted Repeats

Hairpin DNA molecules are then formed from the inverted repeats. Generally, DNA hairpin molecules are formed from inverted repeats by denaturation followed by renaturation. A preferred process for forming hairpin DNA molecules is by rapid intrastrand annealing at low effective DNA concentration. Following ligation and denaturation of the DNA ligase, crosslinks are reversed, linear DNA is extracted, linear DNA is enriched and the sample is heat-denatured and rapidly renatured. Denaturation and renaturation are preferably carried out under volume and buffer conditions that promote intramolecular over intermolecular annealing. Denaturation and renaturation are also carried out under conditions that allow annealing between homologous sequences but discourage annealing between non-homologous sequences. These objectives can be achieved for example, by varying the salt and formalin concentration in the denaturation/renaturation buffer. Head-to-head ligation products between homologous sequences generates inverted repeats (IRs) which undergo intrastrand reannealing into double stranded dsDNA hairpin molecules when denatured and rapidly renatured (a process periodically referred to herein as "snapback"). Ligation products between non-allelic segments and unligated DNA fragments remain single stranded.

Dependent upon the particular technique for forming hairpin molecules from inverted repeats, nonlimiting examples of agents for forming hairpin molecules include agents used in one or more of heat denaturation followed by rapid reannealing or isothermal hybridization approaches.

Forming Single Stranded DNA Molecules

Single stranded DNA molecules that do not contain inverted repeats remain or otherwise result after forming hairpin molecules from inverted repeats.

Separating Single Stranded DNA Molecules from Hairpin DNA Molecules

In a subsequent operation, the single stranded DNA molecules are separated from the hairpin DNA molecules, thereby enabling detection of pairing between homologous DNA sequences. Separating the single stranded DNA molecules from the hairpin DNA molecules can be performed by eliminating single stranded DNA molecules by a single strand specific nuclease. Elimination of single stranded DNA by a single strand specific nuclease, for example S1 or P1 nuclease, with concurrent preservation of DNA sequences involved in hairpin DNA molecules results in specific enrichment of sequences engaged in homologous pairing. Additional nonlimiting examples of single strand specific nuclease include Mung Bean Nuclease and Exonuclease I. In addition, single stranded DNA can be separated from double stranded DNA by adsorption of the snapback treated sample to BND cellulose followed by elution under conditions that specifically elute double stranded DNA. BND cellulose is benzoylated naphthoylated DEAF cellulose. DEAE cellulose is diethylaminoethyl cellulose, and is a positively charged resin used in ion exchange chromatography. BND cellulose is also a resin used in ion exchange chromatography. In the preferred embodiment, a round of denaturation and renaturation followed by adsorption of single stranded DNA to BND cellulose is followed by a second round of denaturation and renaturation followed by S1 nuclease digest. Thus, the HPC assay specifically enriches for DNA segments engaged in homologous pairing.

Amplifying Remaining Hairpin Molecules

Optionally, after performing such separation of the single stranded DNA molecules from the hairpin DNA molecules, the remaining hairpin DNA molecules may be subjected to an amplifying operation. Examples of such amplifying operations include but are not limited to linker-mediated polymerase chain reaction and ligation-mediated amplification.

Applications of the HPC Assay to Different Interactions

Figure 2:
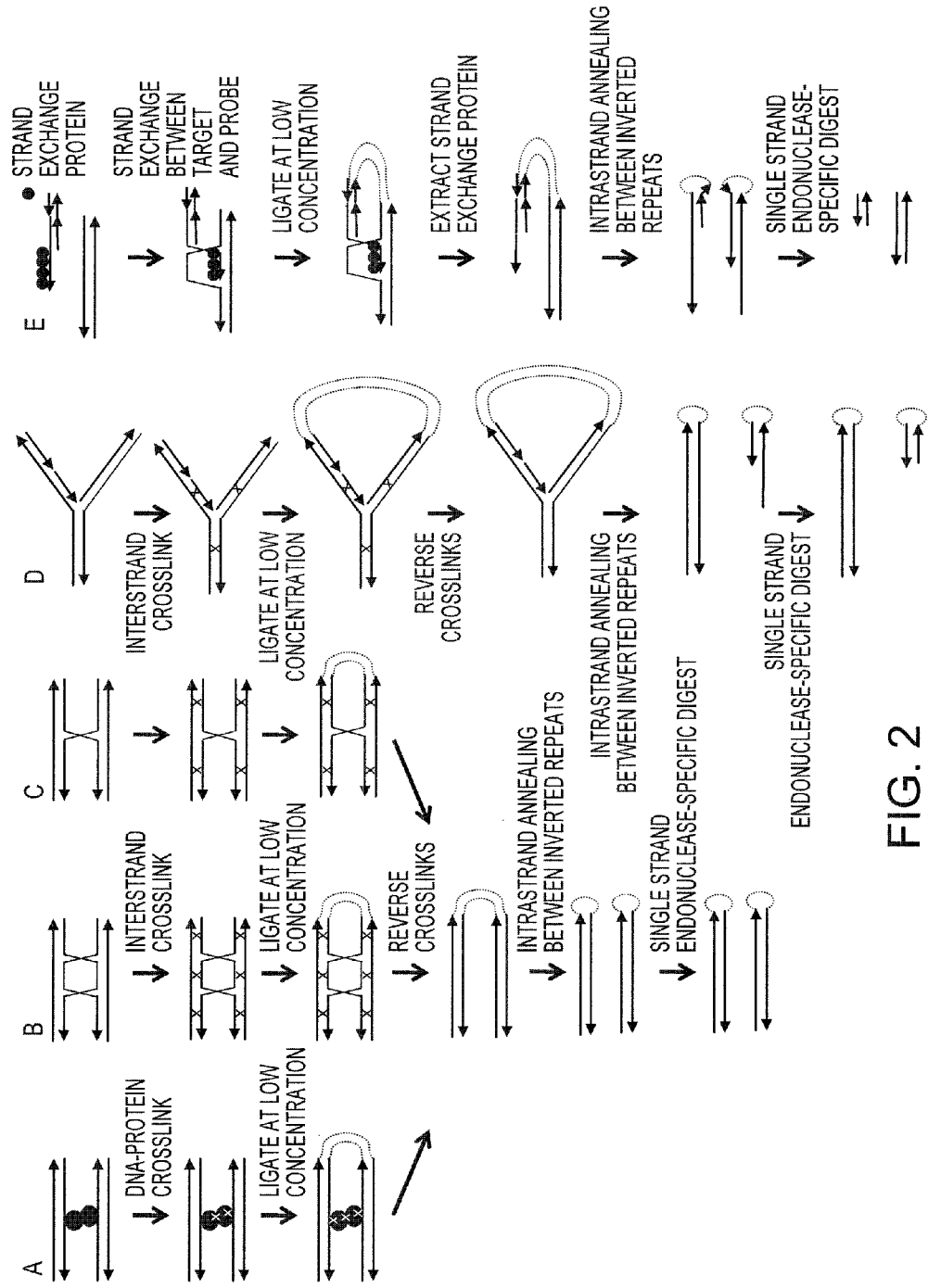
FIG. 2 schematically illustrates various applications of the HPC assay.

Protein-Mediated Pairing, Double and Single Holliday Junctions, Replication Forks, and Strand Invasion Intermediates Overall, the HPC assay can be used to detect pairing interactions mediated by proteins or other spatial constraints, 4-armed homologous sequences connected by single or double Holliday junctions, or 3-armed homologous sequences connected by strand invasion events or replication fork intermediates. FIG. 2 summarizes various applications for the HPC assay.

Specifically, the HPC assay can be used for detecting interactions between sister chromatids in mitotically growing cells or cells arrested at a cell cycle stage during or after replication. The HPC assay can further be used to detect segments of preferential interactions between homologous chromosomes in diploid cells and during meiosis. The HPC assay can be used to detect any branched DNA molecules from which three or four DNA arms are emerging, two of which are homologous to each other. Such branched DNA structures include single Holliday junctions, double Holliday junctions, and replication forks. Holliday junctions arise at loci where recombination occurs preferentially. Since double Holliday junctions are precursors that specifically give rise to crossovers, by identifying the sites of future crossovers, a genetic map can be established. This mapping could be quantitative and predict how often certain positions along a chromosome would be separated from each other by recombination. Establishing sites of recombination and recombination frequencies are important features of genetic maps. Importantly, mapping Holliday junctions enables the generation of genetic maps independent of the availability of genetic markers.

Referring to strategies A-E illustrated in FIG. 2, once head-to-head ligation products of homologous DNA have been generated, enrichment of these sequences proceeds identically in all cases. First, crosslinks are reversed, such as in the case of formaldehyde crosslinking by incubation at 65° C. overnight. Second, supercoils are removed from circularized DNA molecules by treatment with a nicking agent, such as a nicking endonuclease, or by incubation with topoisomerase. It will be appreciated that a wide array of nicking agents can be used. An alternative approach for removing circularized, supercoiled ligation products is 2D gel electrophoresis where a second dimension in the presence of ethidium bromide and at high voltage results in decreased electrophoretic mobility of circular molecules. Following electrophoresis in the second dimension, the arc of linear molecules is excised from the gel and eluted. Third, DNA is denatured and rapidly renatured, generating DNA hairpins in the case of inverted repeat ligation products. Fourth, single stranded DNA is removed or eliminated, for example by incubation with a single strand specific nuclease (S1, P1) or by adsorption to a matrix that specifically binds ssDNA, for example benzoyl naphthoyl DEAE Cellulose.

Strategy A illustrates protein mediated homologous pairing. This strategy enables detection of transient or stable interactions between homologous sequences mediated by proteins by HPC. To detect protein-mediated pairing, interactions are stabilized by crosslinking with a reversible DNA-protein crosslinking agent such as formaldehyde. If pairing interactions are sufficiently stable to survive cell lysis without further stabilization, crosslinking can be omitted. Crosslinking would typically take place in intact cells. Stabilization or crosslinking is followed by cell lysis. Fragmentation of DNA can occur via one of several methods, for example by use of a restriction enzyme, sonication, adaptive focused acoustics (AFA), or enzymatic, sequence non-specific fragmentation (Fragmentase). Ligation of fragmented DNA is preferably carried out at low concentration, typically at about 1 ug/ml. If sequence-non-specific methods of DNA fragmentation are used, DNA ends are filled up with T4 DNA polymerase or Klenow fragment to generate blunt ends of DNA and adsorption to BND cellulose is omitted. Reference molecules include DNA from the same cell sample where ligation was omitted or ligation was carried out following reversal of crosslinking and extraction of genomic DNA.

Strategies B and C illustrate detection of single or double Holliday junctions. Double Holliday junctions (strategy B) and single Holliday junctions (strategy C) are key recombination intermediates of homologous recombination, in eukaryotes during meiotic recombination and DNA repair and in prokaryotes during DNA repair and exchange of DNA between bacteria, for example during conjugation. Since Holliday junctions are intermediates of meiotic recombination that are likely processed into crossovers, the frequency of Holliday junctions should correlate with the frequency of crossovers. The preferred embodiment HPC assay can be used to map the localization of four armed recombination intermediates between homologous sequences. To detect Holliday junctions, they are stabilized by incubation with a reversible crosslinking agent such as UV-activated psoralen or by DNA extraction under conditions that minimize branch migration, for example DNA extraction in the presence of divalent ions using the detergent CTAB and absence of chelating agents such as EDTA or the ethidium bromide which promotes branch migration of Holliday junctions and loss of branched molecules that entail Holliday junctions. Following stabilization of strand invasion intermediates in vivo or in vitro, DNA fragmentation, end polishing and DNA ligation are carried out as described in strategy A. Ligation is followed by a reversal of crosslinking or mobilization of Holliday junctions, for example by addition of EDTA and incubation at 65° C. All steps for enrichment for head-to-head ligation products are carried out as described above. Reference molecules in this case include the same DNA sample ligated without prior stabilization of branched recombination intermediates.

In strategy D, enrichment for sequences containing replication forks is illustrated. Three-armed DNA molecules that involve two homologous arms, as they are found in replication forks or strand invasion intermediates, can be detected by the HPC assay. Such three-armed intermediates are stabilized by special extraction procedures that prevent strand migration, for example by psoralen crosslinking, CTAB extraction or isolation from agarose plugs and that can be reversed following ligation. Fragmentation, ligation at low concentration and extraction are carried out as described in strategy A, followed by the common steps for strategies A-C (see above).

Strategy E illustrates detection of specific DNA sequences in a complex mixture of DNA. This application of the HPC assay involves the detection of one or multiple DNA sequences in a complex mixture of DNA. Probes of DNA carrying a single stranded 3' overhang are pre-incubated with a DNA exchange molecule such as RecA. The pre-assembled nucleoprotein filament is subsequently added to the complex mixture of DNA to be analyzed. To prevent completion of strand exchange, a non-homologous tag is attached to the probe DNA molecule. Accordingly, the strand invasion does not proceed along the entire molecule. Following strand invasion under optimized conditions, the strand invasion intermediate specifically forms between the probe and its homologous target DNA. The three-armed structure of the strand invasion intermediate is ligated at low concentration, and ligation products are treated as described under common steps for strategies A-E.

Diagnostic Applications

In other embodiments, the HPC technology of the present invention finds use in diagnostic applications. For example, in some embodiments, HPC methods are used to determine the pairing status of a gene of interest. Certain disease states are characterized by aberrant (e.g., increased or decreased) pairing that correlates at some states of development or in some cell types. Such diseases may include but not be limited to conditions of defective parental imprinting or chromosomal dosage compensation. HPC methods thus find use in the diagnosis of such disease states by detecting these patterns. In some embodiments, HPC is used to compare the interaction profiles of genes in the activated or inactivated states with test samples in order to determine the activation status of a gene.

In still other embodiments, HPC is used in the detection of variant (e.g., polymorphic) genes that have altered expression.

In yet other embodiments, HPC is used to detect patterns of chromatin interactions that are indicative of genomic rearrangements. In some embodiments, HPC is used to compare the interaction profile of known gene rearrangements with test samples in order to determine the chromatin interactions of the variant gene, which can in some case be correlated with the activation status of a gene at some stage of development or in some cell types.

In additional embodiments, diagnostic signatures are utilized. In some embodiments, diagnostic signatures give information about diagnostic predisposition and prognosis regarding specific diseases. For example, in some embodiments, diagnostic signatures predict future genomic rearrangements or detect chromosome conformation features associated with particular disease states or prognosis. In some embodiments, diagnostic signatures to be used as controls (e.g., indicative of a given disease state or prognosis) are experimentally generated using, for example, the methods of the present invention.

Research Applications

In yet other embodiments, the HPC methods of the present invention find use in research applications. Such applications include, but are not limited to, the study of gene regulation in development and differentiation, the study of gene regulation in disease, the study of gene regulation in drug metabolism, and the study of regulation of variant genes. In some embodiments, research applications utilize samples from human subjects. In other embodiments, research applications utilize test samples from non-human animals (e.g., non-human mammals). In some embodiments, the non-human animals are transgenic animals.

Kits

In yet other embodiments, the present invention provides kits for performing HPC. The term "kit" as used herein refers to a collection or assembly of components and/or agents that are preferably packaged together, sold together, distributed together, and/or purchased together. Preferably, the components and/or agents are typically provided in a common container or packaged set. However, the invention also includes arrangements in which the kit is packaged in two or more subpackages, sold in portions, distributed in portions, and/or purchased in portions. In some embodiments, the kits contain all of the components necessary or sufficient for performing HPC analysis of closely juxtaposed pairs of homologous DNA segments and particularly in cells, including all controls, directions for performing assays, and any software for analysis and presentation of results. In some embodiments, the kits contain primers for performing HPC analysis. In some embodiments, the kits comprise all materials necessary or sufficient to perform HPC in a single reaction and provide diagnostic, prognostic, or predictive information (e.g., to a researcher or a clinician). In some embodiments, the kits comprise one or more of a polymerase (e.g., a thermostable DNA polymerase), a ligase (e.g., a thermostable ligase), primers for amplifying the products of a ligase chain reaction, buffers, control reagents, sequencing reagents, solid surfaces for analysis, microarrays for analysis, detection devices, software, instructions, and control genomic interaction libraries.

In some embodiments, the kits comprise all of the components for generating and utilizing a diagnostic signature (e.g., to provide a diagnosis or prognosis) or interaction profile of a sample. For example, in some embodiments, the kits comprise control diagnostic signatures or interaction profiles and software and/or instructions for comparing a test sample to the control.

The kits may also comprise any one or more of the following. The kits may include a buffer solution or agent(s) for use in forming head-to-head ligation products. The kits may also include a buffer solution or agent(s) for use in forming hairpin molecules. The kits may also include a prepacked column and/or charged resin for selectively separating single stranded DNA species from hairpin molecules. Preferably, the charged resin is BND cellulose.

EXAMPLES

Enrichment of an Endogenous, cis-Located Inverted Repeat

In the HPC assay, coaligned homologous sequences are converted into inverted repeats as a prerequisite of subsequent selective enrichment, see FIG. 1. To evaluate whether the HPC assay selectively enriches for an inverted repeat from a complex mixture of genomic DNA, a "2-micron" plasmid was used. This plasmid is a nuclear plasmid endogenous to most S. cerevisiae strains at approximately 50 copies per cell. Importantly, the 2-micron plasmid carries an interrupted inverted repeat, with two approximately 600 bp head-to-head repeat units flanked by about 1.2 kb and about 3.9 kb of non-repetitive sequences, see arrows of FIG. 3A. Appropriately linearized 2-micron plasmid structurally resembles paired homologous sequences ligated in a head-to-head orientation, see FIG. 3B. If the HPC assay preserves paired/ligated but not unpaired/non-ligated homologous sequences, the repeat region should be selectively preserved in an NcoI-linearized plasmid, where the repeats are connected as depicted in FIG. 3B; but should be destroyed when the connection between the repeats is severed, for example by an EcoRI digest, as shown in FIG. 3C.

Figure 3:
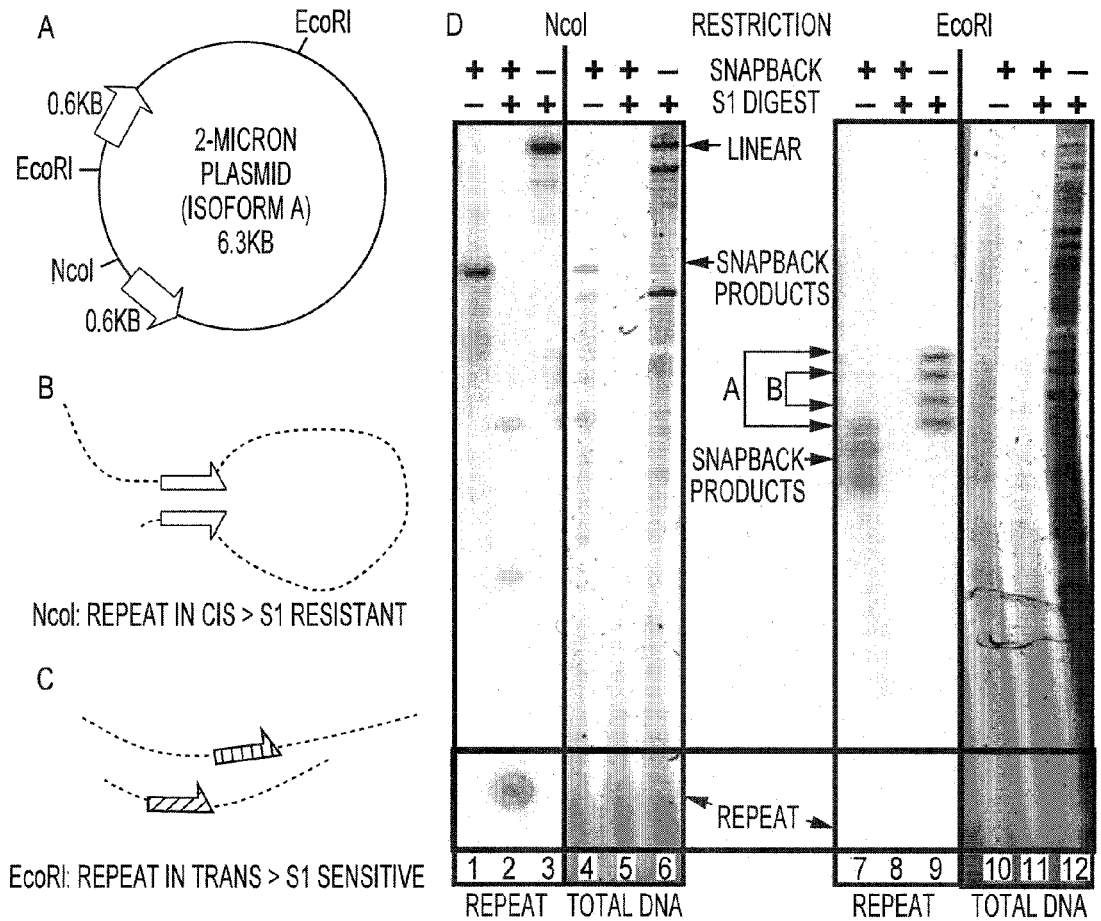
FIG. 3 schematically illustrates intrastrand reannealing of 2 micron plasmid.

To examine whether the HPC assay preserves paired versus unpaired homologous sequences, genomic yeast DNA containing 2-micron plasmid was digested with NcoI or EcoRI. Both restricted DNA samples were subjected to three alternative treatments, as shown in FIG. 3D. These three treatments are as follows: (i) Intrastrand reannealing at a NaCl concentration previously optimized for reannealing ("snapback"), (ii) snapback followed by S1 digest, and (iii) S1 digest without prior snapback. Although not shown, conditions for S1 digest had previously been optimized to eliminate most ssDNA while preserving dsDNA. For both NcoI- or EcoRI-digested samples, snapback+S1 treatment results in elimination of bulk genomic DNA, while genomic dsDNA including the plasmid stays intact when snapback prior to S1 digest is omitted. See ethidium bromide-stained agarose gel, lanes 5, 6 and 11, 12 illustrated in FIG. 3D. By contrast, the repeat region (600 bp) is largely preserved when both repeat halves reside on a single restriction fragment such as in FIG. 3B, lane 2; but degraded when the repeat halves are separated in an EcoRI digest, such as in FIG. 3C, lane 8; as indicated by Southern analysis with a repeat-specific probe. Thus, the snapback procedure selectively preserves an inverted repeat when localized in cis, but destroys it when localized in trans. Referring further to FIG. 3, the EcoRI digest generates two 2-micron isoforms (A and B) present at equimolar levels and differing by inversion of the unique plasmid regions indicated in lane 9. Together, these results have three important implications: (i) the snapback plus S1 treatment specifically enriches for head-to-head arranged repeats residing on the same molecule, (ii) even repetitive DNA (>50 copies/cell) is efficiently eliminated by snapback+S1 treatment when localized in trans, i.e. when the two repeats have been separated by EcoRI digest, and (iii) looped out inter-repeat regions are eliminated along with bulk genomic DNA by snapback+S1 treatment.

Conversion of Crosslinked, Ligated Genomic DNA into S1 Sensitive ssDNA

Efficient intramolecular ligation of formaldehyde-crosslinked chromatin and snapback elimination of non-repeat DNA was further optimized in three fashions. First, the volume for ligation was optimized by monitoring circularization versus multimerization of a particular phage lambda EcoRI fragment. Circularization was determined based on circular versus linear electrophoretic mobility of that fragment.

Figure 4:
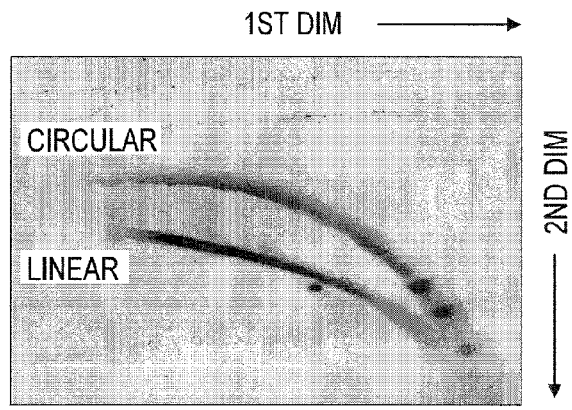
FIG. 4 illustrates 2D-gel analysis of genomic DNA from cells crosslinked with 0.75% formaldehyde, EcoRI digested and ligated.

Second, ligation efficiencies of crosslinked chromatin were monitored. Besides inter-molecular ligation products involving ligated sister chromatid or non-allelic regions, crosslinked chromatin fragmented with a restriction enzyme such as EcoRI also generates circular ligation products by intra-molecular ligation. The abundance of such restriction fragments circularized by ligation under different crosslinking conditions was monitored to assess restriction and ligation efficiencies of formaldehyde-crosslinked chromatin. It has been previously reported that on a 2D gel, circularized DNA migrates slower when ethidium bromide is included in the 2nd dimension, generating an arc of circles that migrates above the arc of linear DNA fragments. In the present analysis, 2D gel analysis of five ligation reactions (genomic DNA; 0.0%; 0.5%; 0.75%; 1.0% formaldehyde-crosslinked chromatin), indicates that restriction/ligation occur with similar efficiencies on <1.0% formaldehyde crosslinked chromatin versus naked genomic DNA, with >⅓ of genomic DNA shifted to the circular arc. FIG. 4 shows 0.75% formaldehyde-crosslinked, EcoRI restriction digested and ligated chromatin. At 1% formaldehyde, circular products are reduced to approximately ¹/₁₀ of total DNA (not shown).

Figure 5:
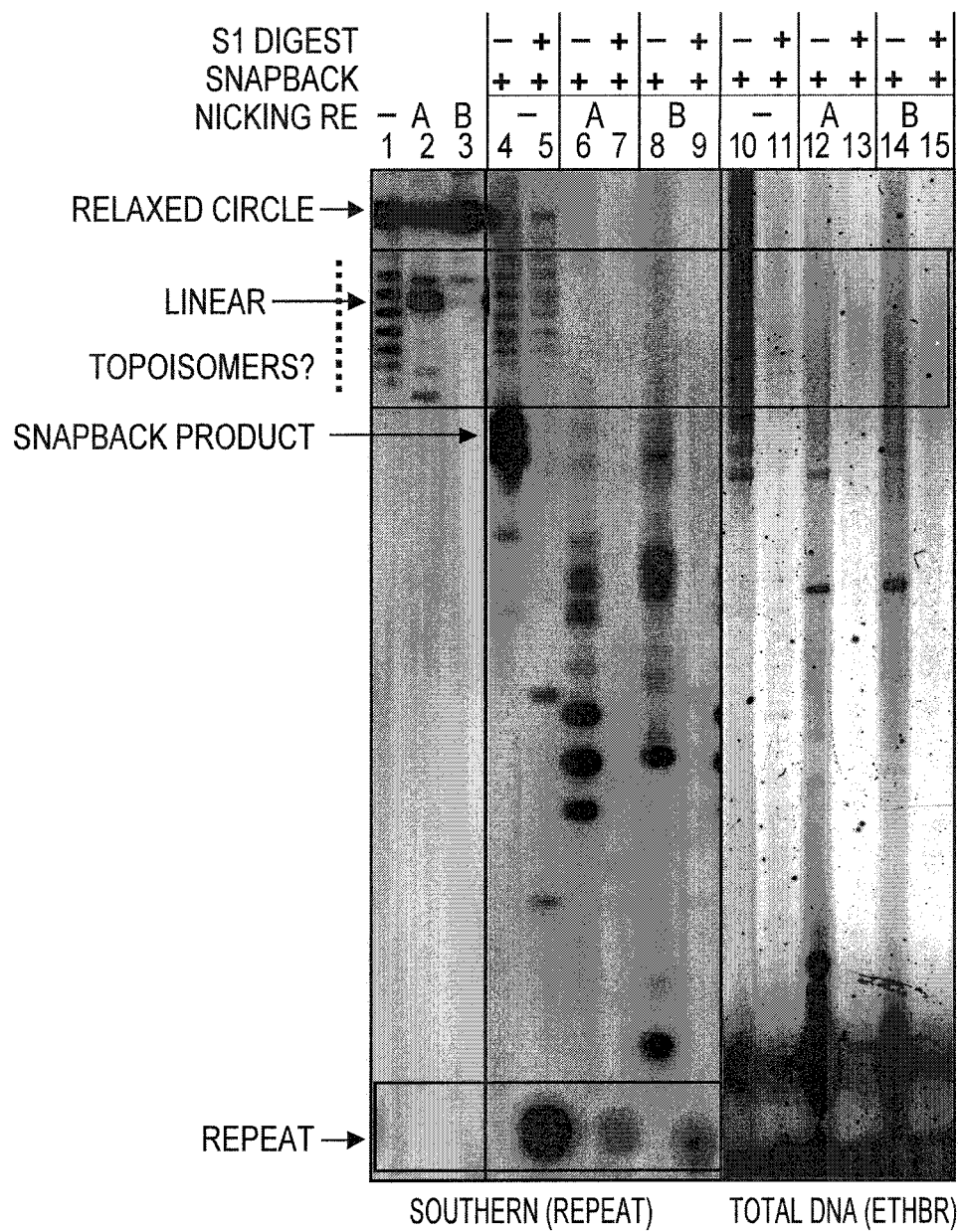
FIG. 5 illustrates elimination of topoisomers by nicking.

Third, measures were undertaken to ensure that the HPC assay efficiently eliminates non-inverted repeat DNA also after in vitro ligation. Following ligation of NcoI-restricted genomic DNA in a large volume, the 2-micron plasmid predominantly migrates as a relaxed circle, but in addition, presumed plasmid topoisomers are formed, as previously demonstrated for in vitro ligation, see FIG. 5, lane 1, top box labeled "Topoisomers?". Such topoisomers are not fully eliminated by S1 treatment following snapback. Likely, they cannot be separated into ssDNA, see lanes 4, 5 of FIG. 5. S1-resistant DNA that does not contain an inverted repeat would potentially affect the signal:noise ratios of the HPC assay. Therefore, attempts were made to eliminate topoisomers by pre-treating NcoI digested, ligated genomic DNA with two nicking endonucleases (NE), Nt.AlwI (=A) and Nt.BsmAI (=B) which introduce a site specific nick into dsDNA. With 5 bp recognition sequences, these enzymes are expected to cut the yeast genome approximately every 1 kb. Incubation with Nt.BsmAI converted 2-micron topoisomers into relaxed circles as shown in lane 3, without linearizing the plasmid, as observed for Nt.AlwI, see lane 2. Consistent with elimination of topoisomers, such species are not detected in Nt.BsmAI-pretreated samples following snapback+S1 treatment, shown in lane 9, while the repeat region is still detectable at substantial levels. Background reduction is also apparent on the ethidium bromide stained gel. Compare lanes 11 and 15. By contrast, treatment with Topoisomerase I failed in this particular experiment. Together, these data demonstrate that crosslinked chromatin can be efficiently fragmented with EcoRI, ligated, and DNA carrying inverted repeats is specifically enriched.

Sister Pairing Along Metaphase Chromosomes

The yeast, S. cerevisiae is uniquely suited for an intersister association assay. First, yeast can be grown as haploid cells, with sister chromatids as the only homologous sequence available. Second, cells can be efficiently arrested at the G2/M stage. Third, the localization of cohesins has previously been mapped at high resolution. The entire HPC protocol was performed on metaphase-arrested cells, using a haploid yeast strain previously analyzed for genome-wide association of cohesin. Cultures arrested at G1 via the alpha factor pheromone were released into medium containing nocodazole, a spindle-destabilizing drug. Both arrest conditions occurred at >90% based on cell morphologies. Following crosslinking with formaldehyde (0.75%), cells were lysed, digested with Fragmentase which had been optimized to digest genomic DNA to generate fragments 1 to 5 kb in length, followed by heat-inactivation of the enzyme, endpolishing with Klenow fragment plus T4 DNA polymerase and ligation of chromatin at low concentration. Crosslinking was reversed, and restriction/ligation efficiencies were assayed by 2D gel, as shown in FIG. 4. Linear ligation products were eluted from the gel. As a reference, the same sample of cells was treated identically, but ligation at low DNA concentration was carried out after reversal of formaldehyde crosslinks and protein extraction, or ligation was omitted. Samples were split and subjected to S1 digest with or without prior snapback ("SB+S1" or "S1" respectively). Subsequently, samples were digested with MseI to open hairpins/generate linker ligation sites, and amplified by LM-PCR (not shown). Equal amounts of the two LM-PCR products were labeled with two different fluorescent dyes and mixed for microarray analysis (not shown). Comparative genomic hybridization (CGH) was performed with the sample ligated before reversal of crosslinking and DNA extraction and two reference samples, one where ligation was carried out after removal of crosslinks and DNA extraction and the other where ligation of crosslinked DNA was omitted. For each condition, SB+S1-treated samples (enriched for ligated head-to-head homologous sequences) were labeled with Cy3 while the sample representing total genomic DNA (S1) was Cy5 labeled. Mixed Cy3-/Cy5-labeled LM-PCR products were hybridized to Agilent tiling microarrays with 44,000 oligonucleotide probes. The average probe length was 55 bp with an average spacing of 250 bp, covering most of the yeast genome, including intergenic regions which frequently represent cohesin binding sites. Probe-labeling, hybridization and microarray scanning were carried out at the Whitehead Institute Genomic Core.

Figure 6:
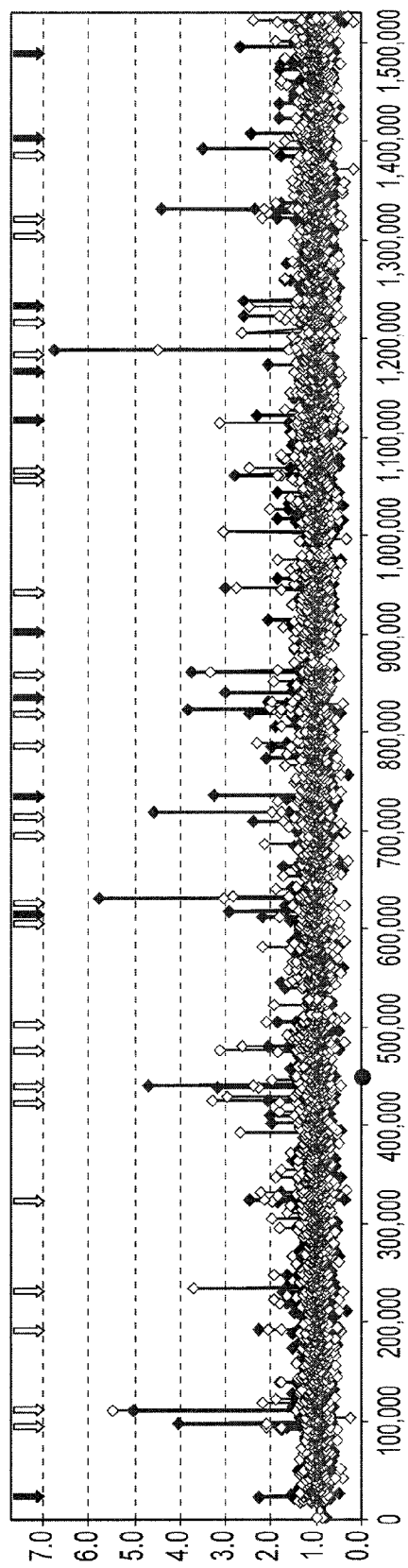
FIG. 6 illustrates pairing profiles along the entire length of yeast chromosome IV, determined by the HPC protocol using Fragmentase and a single round of snap back.

Presumed sister chromatid pairing sites were identified by determining the (SB+S1)/(S1 only) ratios for each oligo in the sample ligated before reversal of crosslinking and protein extraction and subtracting from it the corresponding ratio of the sample that had been ligated after reversal of crosslinks and protein extraction. FIG. 6 shows SB-ratios for oligos along the entire length of chromosome IV, which comprises approximately ¹/₁₀ (1,500 kb) of the yeast genome. Peaks are defined at positions where an oligo element on the microarray in the sample ligated before extraction is enriched versus the sample where ligation was omitted (grey) or carried out after reversal of crosslinks and extraction of DNA. Black arrows with grey fill indicate positions where signals at the same oligo were enriched at least 2-fold in the sample versus both references while black arrows indicate positions where enrichment is only observed in the test sample versus the reference sample where ligation was carried out after reversal of crosslinking and DNA extraction, see FIG. 6. Sequence positions are given in by based on sequence information in Agilent oligonucleotide annotation.

A total of 34 oligos of 5267 oligos along chromosome IV were reproducibly detected along the length of chromosome IV. These results have four important implications. First, the HPC assay detects crosslinking-dependent peaks at a high resolution, indicating that this assay can be applied to detect homologous pairing in vivo. As far as is known, the HPC assay is the first assay that detects in vivo homolog associations on a molecular level. Second, sister pairing is limited to a small set of positions along chromosomes, covering ~30 sites on average <500 bp in length (oligos are spaced with an average distance of 250 bp). Thus, sister chromatids are not uniformly coaligned, but are paired only at a limited number of short regions which are separated by extensive regions without substantial pairing. Third, at metaphase, sister chromatids are frequently juxtaposed at homologous regions rather than being organized out of register. By implication, sister chromatids follow symmetrical, convergent paths within the volumes of condensed chromatids, rather than being randomly packaged.

Determinants of Pairing Between Sister Chromatids

The pairing status of centromeres is uncertain. Despite high levels of cohesin at and around the centromere, apparent centromere separation has previously been observed in living cells. The HPC data described herein indicate that pairing at centromere IV is low, but a strong pairing site is detected at 441 kb, approximately 10 kb upstream of CenIV which is located at 450 kb, consistent with weak pairing at the centromere, but strong pairing in pericentromeric regions. Together, these results indicate that regions of sister coalignment frequently coincide with cohesin binding sites, consistent with a role of a subset of cohesins in close sister chromatid juxtaposition. Different physical requirements of different pairing sites provide motivation for genetic analysis of potential different pairing pathways.

Figure 7:
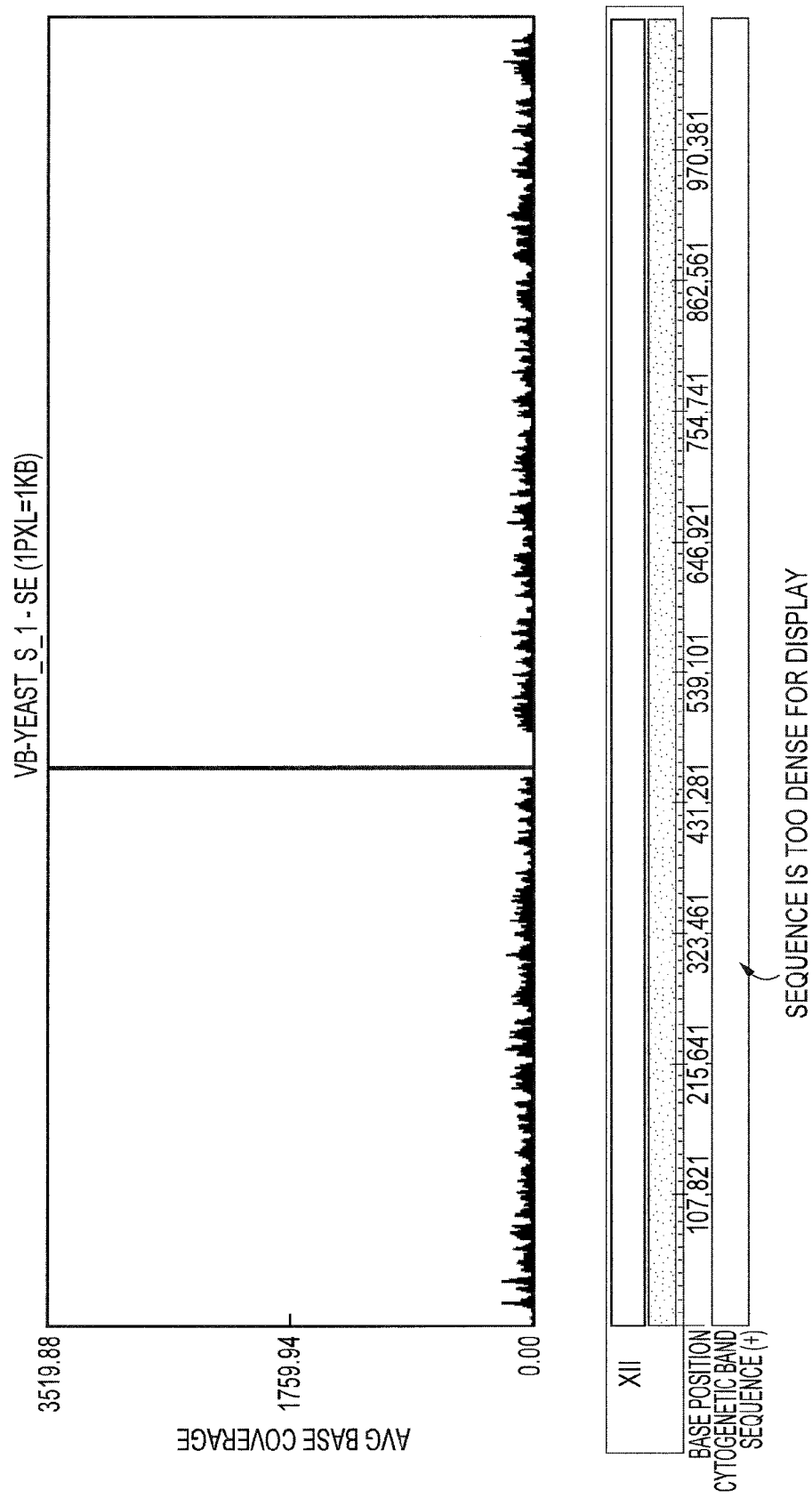
FIG. 7 illustrates the pairing profile of the entire yeast (*S. cerevisiae*) chromosome 12, generated by EcoRI digestion of chromatin followed by a first round of snap back and adsorption of single stranded DNA to BND cellulose and second round of snapback followed by incubation with S1 nuclease. Peaks indicate the frequency of sequencing reads in Illumina sequencer. Chromosome 12 is represented by approximately 800,000 reads.

In a second experiment, the haploid yeast strain was arrested in G2/M using the microtubule depolymerizing agent nocodazole, and cells were crosslinked using 0.75% formaldehyde. Following removal of cell walls with zymolyase, cells were lysed and crosslinked chromatin was incubated with the restriction enzyme EcoRI. Following inactivation of EcoRI, the EcoRI-digested chromatin was ligated at low concentration to minimize intermolecular ligation between DNA fragments not cojoined by a crosslinking interaction. Crosslinking was reversed, DNA was extracted and linear DNA including head-to-head ligation products were separated from circular DNA by 2D gel electrophoresis. The arc containing linear DNA was extracted from agarose. DNA was denatured by boiling for ten minutes in 50% formamide and 50 mM NaCl and rapidly renatured by incubation on ice. DNA was mixed with equilibrated BND cellulose and incubated for five minutes at room temperature. Double stranded DNA was eluted with a buffer containing 10 mM Tris, 0.1 mM EDTA, 1M NaCl. DNA was precipitated and dissolved again in 50% formamide and 50 mM NaCl followed by a second snapback procedure. The second round of snapback was followed by digestion with S1 nuclease, resulting in further elimination of contaminating single stranded DNA. DNA was restriction digested with MseI, the DNA ends were made blunt using an endpolishing kit, and Illumina linkers were added. Following enrichment of fragment sizes between 150 and 500 bp by agarose gel electophoresis, the sample was PCR amplified and sequenced by Illumina sequencing. The sample generated >11 million yeast sequences which were aligned to S. cerevisiae genome using Illumina software. FIG. 7 shows the sequence profile for chromosome 12. Comparison of this profile to a profile derived from a reference sample where DNA ligation is carried out following reversal of crosslinking and DNA extraction instead of before will identify the pairing sites between sister chromatids. A high peak in the profile of S. cerevisiae chromosome 12 entails an 850 bp sequence from chromosome coordinates 459,750 to 460.600. This sequence corresponds to 850 bp of the 9,000 bp rDNA repeat that is present at a copy number of >150 in the yeast genome. Exclusive preservation of these 850 bp with concurrent elimination of the remaining sequence of the rDNA repeat cluster indicates that pairing between homologous sequences in the rDNA cluster is limited to this segment of the rDNA.

Preliminary studies demonstrate the feasibility of pairing analysis at the molecular level via the HPC assay. The HPC assay can be optimized and validated by molecular and cytological approaches for mapping pairing sites at several developmental stages, including mitosis and meiosis. It is believed that pairing occurs at discrete sites, separated by regions where pairing is low or absent.

Homologous Pairing Capture (HPC) Assay Protocol Optimization

In a first aspect, modified fragmentation was investigated. Preliminary studies identify sister pairing sites along metaphase yeast chromosomes. To ensure comprehensive pairing detection, (i) sequence-independent genome fragmentation is introduced, ensuring similar ligation and intrachain reannealing properties for all genome regions and (ii) physical instead of enzymatic chromatin fragmentation is undertaken. Adaptive focused acoustics (AFA) provides superior control of genome fragmentation, generating chromatin fragments with appropriate length, i.e. >1 kb. In certain embodiments, this alternative fragmentation approach can be utilized. AFA induces breaks at non-allelic positions in cojoined sister chromatids, and ligation would generate interrupted inverted repeats. It is not expected that this will interfere with the HPC assay. Preliminary studies applying HPC to an interrupted inverted repeat on the 2-micron plasmid demonstrates S1 resistance of the repeat region, but degradation of looped out non-repeat regions. To achieve efficient ligation, end-polishing of AFA-fragmented chromatin for ligation could be performed following established protocols of combined T4 DNA polymerase/T4 polynucleotide kinase treatment. Ligation efficiencies could be examined by 2D gel analysis. Fragmentation to approximately 2 kb would ensure >1 kb overlaps between most homologous sequence segments, ensuring efficient and unbiased detection of homologous pairing. In the event that AFA fragmentation proves unfeasible due to for example low ligation efficiencies, efforts could be undertaken to fragment chromatin using Fragmentase (see above; available from New England Biolabs), an enzyme mix of a sequence independent nicking agent and a second strand cleaving enzyme. While enzymatic, this approach of chromatin fragmentation is still sequence-independent, making it superior to restriction digest. As a third option, efforts to perform digests with one or two other site-specific restriction endonucleases, such as HindIII and BgIII could be undertaken which have previously been used for 3C. Lastly, attempts to adjust the HPC protocol for high throughput sequencing have been undertaken. This approach avoids hybridization artifacts and unequal sensitivities for different probes.

Controls.

To validate the HPC assay, four additional controls can be introduced: (i) Crosslinked G1-arrested cells could be analyzed along with G2/M arrested cells, (ii) Ligation could be omitted in the crosslinked sample, (iii) Ligation of non-crosslinked samples could be carried out after, rather than before crosslink-reversal and DNA extraction, and (iv) A Cy3/Cy5 color-swap could be introduced for all microarray hybridizations. Controls (i) and (ii) will exclude from further analysis sequences protected independent of ligation or of a sister chromatid, for example due to cryptic inverted repeats. Control (ii) will further ensure that snapback is ligation mediated rather than by incomplete crosslink reversal. Control (iv) will exclude effects of differential Cy3 versus Cy5 fluorescence decay. Control (iii) will examine whether peaks observed in the preliminary studies in the non-crosslinked sample, disappear when ligation is carried out after protein removal. If peaks disappear when ligation is carried out after protein removal, this would indicate the existence of a special subset of interactions that is stable without crosslinking. Such pairing interactions may exhibit different cis- or trans-determinants, an important consideration for bioinformatic or mutational analysis. If the peaks are present both when ligation is carried out on non-crosslinked chromatin and extracted DNA, this would suggest that such interactions are not protein-mediated. In that case, a search could be intensified for cryptic inverted repeats in these molecules to exclude alternative explanations, for example protein independent pairing interactions.

Validation of Pairing Sites and Pairing-Free Regions

In this aspect, microarray- and LM-PCR independent molecular validation of pairing sites were investigated. Following reproducible detection of sister pairing using the revised protocol, sister pairing sites and non-pairing sites could be validated by Southern analysis of LM-PCR products. Probes could be generated against pairing and against non-pairing regions. Pairing sequences should be specifically enriched in PCR products derived from snapback plus S1 treated, crosslinked samples compared to non-snapback treated samples and compared to non-crosslinked samples ligated after crosslink-reversal and DNA extraction. S1 digest is included in all samples to account for S1 hypersensitive genome regions. A non-pairing sequence probe, by contrast, should yield a less intense signal in the SB+S1-derived PCR product versus the equivalent non-SB treated control sample. Thus, pairing-free regions should be specifically depleted in the "snapback-plus-S1" samples.

Pairing and pairing-free sequences can be validated via dot blot analysis of a tiling array representing a genome region with appropriate pairing peaks and valleys. Yeast genomic DNA resistant to appropriate variations of snapback and S1 treatment can be labeled with $^{32}$P and hybridized against a hand-made tiling array with saturating amounts of DNA sequences. If AFA-fragmented samples can be used for the modified experiment, no hairpin opening of probe DNA is required since looped out hairpins are eliminated by S1 nuclease, eliminating the hairpin connection between the two sister chromatid derived repeats. Preliminary studies indicate that ligated inverted repeats are preserved at high levels, raising the possibility that enriched sequences can be used as probes with minimal or without amplification. Non-amplified ChIP DNA has previously been used on such DNA arrays, and the HPC protocol can be scaled up to higher volumes to harvest sufficient amounts of DNA for direct Southern analysis. Establishing a dot blot-based detection system for pairing select pairing interactions is useful for subsequent analysis of pairing under mutant conditions.

In this aspect, cytological validation was investigated. Preliminary studies predict the existence of long, pairing-free regions (>50 kb; 10% of an average yeast chromosome), similarly to those previously detected cytologically around the centromere of cells at prometaphase. Arbitrarily selected genome regions are further unpaired in approximately 15% of metaphase cells, and may indicate that unpairing is a more universal feature. Following validation, the pairing status of select regions can be cytologically examined by FISH. Two FISH probes (>7 kb), recognizing sequences at the center of high versus low pairing, can be labeled with different fluorophores, and hybridized to maximally (i.e. lipsol) spread nuclei from cells at various post-replicative stages. Using bar1 cells released from alpha factor (G1) arrest, S-phase progression is then monitored via budding status or FACS, to achieve semi-synchronization of cells. Short spindle status (detected with anti-tubulin antibodies) can be used as metaphase markers. Microscopy can be performed using the integrated DeltaVision Restoration Imaging system (available from Applied Precision, Inc.). Image deconvolution generates high resolution images of spread nuclei. Regions derived from ancient genome duplications are preferably excluded as FISH targets to avoid multiple FISH signals from genome regions that cannot be distinguished by FISH. More frequent postreplicative duplets in pairing-free versus paring region would indicate that the HPC assay indeed detects physical distance between chromatids.

Controls for unpairing preferably include cohesin-mutants arrested at metaphase and/or centromeric regions. Centromeres undergo temporal separation during prometaphase and can be used as an internal control. A mitotic FISH pairing assay targeted to appropriately selected sites will allow cell cycle specific analysis of pairing status and pairing analysis in mutants. Pairing levels have recently been studied by GFP tagged chromosomes which provide superior resolution, but require integration of repetitive sequences which limits the number of sites accessible to analysis, makes concurrent analysis of two or more sequences problematic and could potentially affect pairing status. If FISH, however, proves problematic, the GFP signal can be used to compare pairing status between strains carrying the GFP target sequence at different sites. If predicted unpaired loop regions cannot be confirmed cytologically, the looping index of such regions can be alternatively determined by a 3C analysis, which has already been performed for the pericentromeric region of yeast.

Map Sister Pairing Sites at Different Cell Cycle Stages and at Specialized Genome Positions Cohesins localize to different genomic sites at different cell cycle stages. Their positions are further modulated by transcription and DNA damage. Cohesins are initially deposited at condensin binding sites, but are relocalized to other sites by transcription. Whether such redistribution of cohesin affects pairing is currently unclear. These possibilities can be examined by determining the pairing status of haploid yeast cells at defined cell cycle stages. Mutant and drug induced arrest conditions can be used to apply a physical pairing assay at different cell cycle stages. Conditional mutations in cdc9 (a ligase required during replication), in cdc31 (a spindle body component), in cdc20 (an APC component), and in cdc14 (a nucleolar phosphatase) can be utilized to arrest cells during S-phase, G2, metaphase, and anaphase, respectively, in addition to hydroxyurea-induced S-phase arrest and nocodazole induced metaphase arrest. Chromosomes in these mutants further exhibit different condensation levels, with possible effects on chromosome pairing. Attempts to map pairing sites in wild-type cells synchronized by centrifugation elutriation, that is selecting cells based on size associated with the G1 stage, would further necessitate optimization of the HPC assay to smaller sample sizes.

Generating profiles of pairing at defined stages of the cell cycle indicates to what extent pairing covaries with cohesin position. Several repetitive genome regions, for example, the rDNA cluster or telomeres, undergo delayed sister separation, but the persistence of single copy pairing interactions would have eluded cytological analysis. Identification of persistent pairing in mutant and wild-type conditions potentially identify alternative or redundant pairing mechanisms. Positioning of the cohesin complex further changes in response to transcription status, and DNA damage, and so pairing patterns are preferably examined in 3' terminal regions of particular genes when transcriptionally active or not and by inducing a well positioned HO endonuclease induced break.

Dot blot analysis can be combined with the HPC assay to determine the pairing status of repetitive genome regions not included on standard microarrays, including rDNA, LTR, subtelomeric Y' and X elements, and Ty1 transposable element. Repetitive DNA does not efficiently reanneal when localized in trans under the conditions examined here, as demonstrated for the intermediately repetitive 2-micron plasmid. Assessing pairing of single- versus multi-copy elements should provide insights into (i) the timing of segregation/unpairing at different genomic loci and (ii) potential roles of repetitive sequences at some or all stages of chromosome juxtaposition.

Map Pre-Meiotic and Meiotic Pairing Sites Along Homologous Chromosomes

Whether pairing between homologous chromosomes during meiosis is mediated by primary DNA sequence and/or proteins is currently unknown. Efforts to assay meiotic pairing can be undertaken to identify (i) pairing sites between homologous chromosomes at different stages of meiosis and (ii) modification of pairing interactions between sister chromatids. Experiments can be performed in a meiotic null (mn)-cdc6 mutant where bulk meiotic replication is abolished, yet several meiotic steps, including cohesin (Rec8) loading and the DNA events of homologous recombination, occur apparently normally. In the absence of replication/sister chromatids, the HPC assay should specifically detect interactions between homologous chromosomes. Synchronous meiosis can be induced in diploid mn-cdc6 cells. Pairing sites can be determined using the optimized HPC assay followed by microarray analysis at four stages, i.e. prior to meiotic entry, during replication completion/leptotene, maximum pachytene, and following pachytene exit.

Mitotic experiments are performed in the W303 yeast strain where cohesin binding data are available, yet meiotic experiments can be carried out in the SK1 strain which readily enters synchronous meiosis. By comparing pairing profiles in mitotic and meiotic cells, the extent to which chromosome elements are shared between meiotic and mitotic chromosome alignment can be better understood. If some or all interhomolog pairing sites are distinct from sister pairing sites during meiosis, further analysis can be performed in diploid WT strains eliminating caveats of situations where sister or homologous chromosomes are absent. If interhomolog pairing sites are found to largely overlap with sister pairing sites, subsequent experiments can be performed in the replication deficient background (mn-cdc6). The presumed existence of premeiotic pairing in yeast, detected by cytological analysis, raises an additional issue. Sites of premeiotic pairing can be assayed in G1-arrested premeiotic cells (see above). If premeiotic interhomolog pairing exists, such pairing should be detectable in the mn-cdc6 and/or diploid WT strains. It is of interest to determine to what extent pairing sites between homologous chromosomes before and during meiosis overlap.

Meiotic pairing sites can be validated as described for mitotic chromosomes, including FISH analysis. Meiotic FISH was previously performed at arbitrary sites. Cytological detection of greater average distances between HPC-determined non-paired sites versus paired sites would provide direct support for the looping out of certain chromatin regions along meiotic chromosomes. Importantly, meiotic chromosomes are less condensed than their mitotic counterparts.

Experimental concepts described herein can be transferred with relative ease to organisms exhibiting superior cytological resolution such as mammalian chromosomes. Importantly, the HPC assay can be applied to different organisms with relative ease, motivating future studies of evolutionary conservation of pairing interactions.

Applications and Conclusions

Interactions between closely aligned, homologous sequences (referred to herein as "pairing") are an important determinant of genome stability in somatic cells and in the germ line. During the mitotic cell cycle, sister chromatids are closely associated from replication until exit from metaphase ensuring bipolar sister chromatid segregation. Closely juxtaposed sister chromatids further serve as templates for chromosome break repair via homologous recombination, rendering post-replicative cells more tolerant to breakage. A failure to repair DNA breaks compromises genome integrity. Genome instability, including chromosome breakage, rearrangements and aneuploidy, are key features of cancer, and premature aging. During meiosis, pairing between homologous chromosomes is a precondition for recombination and formation of chiasmata, which provide linkage between homologs ensuring their faithful segregation. During the process of meiotic recombination, homologous DNA segments are closely juxtaposed, and form crossovers via central recombination intermediates where the two DNA strands from homologous chromosomes are connected by strand exchange, called the double Holliday junction.

A central protein axis from which large peripheral chromatin loops emanate constitutes a defining feature of higher order chromosome organization. Sequences at the loop bases are proposed to be involved in close juxtaposition of homologous chromatid regions, yet the molecular identity of such pairing interactions is presently unknown.

Sister Chromatid Coalignment in Somatic Cells

Figure 8:
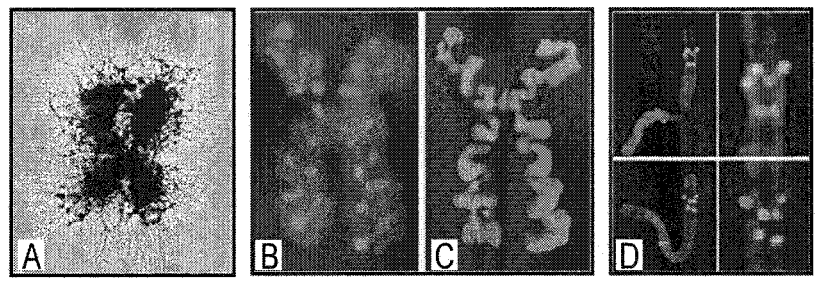
FIG. 8 illustrates metaphase chromosomes.

Coalignment at variable distances between allelic sister chromatid segments is implicit in most models of metaphase chromosomes. Mild spreading of hypotonically treated chromosomes results in partial chromatin unfolding, revealing radial chromatin loops that emerge from an axial protein scaffold. This indicates that the 11 nm primary chromatin fiber is packaged into approximately 700 nm wide metaphase chromatids via several hierarchical folding steps, see FIG. 8A. Whether chromatin within metaphase chromosomes follows a predetermined folding pattern is unclear. Immunostaining of chromosome scaffold proteins (topoisomerase II and condensin), as well as preferential staining of extremely AT-rich sequences reveals a helical, semi-regular coiling path of the chromosome scaffold. Importantly, opposite handedness of sister chromatids is apparent in select preparations of mammalian metaphase chromosomes, see FIGS. 8B and 8C (Maeshima K, Laemmli U K. A two-step scaffolding model for mitotic chromosome assembly. Dev Cell. 2003 April; 4(4):467-80. PMID: 12689587). Conversely, no reproducible folding pattern is obvious from systematic positional analysis of three consecutive GFP tags in a mammalian chromosome, see FIG. 8D (Strukov Y G, Belmont A S. Mitotic chromosome structure: reproducibility of folding and symmetry between sister chromatids. Biophys J. 2009 Feb. 18; 96(4):1617-28. PMID: 19217877). Limitations of cytological assays, including extraction artifacts and small sample sizes are overcome by the HPC assay, which allows parallel analysis in millions of intact cells. Notably, any preferred folding pattern of sister chromatids that involves more intimate association of certain homologous regions will be detected by the HPC assay, providing novel insights into chromosome structure at molecular resolution.

Little is known about the structure of interphase chromosomes. Occupying preferred nuclear territories and possibly retaining some axial organization, their pairing status remains unclear. Sister chromatids undergo cytologically detectable unpairing at several loci during G2, in both plants and humans, with distances reaching 800 nm, corresponding to >10-fold the predicted dimensions of the cohesin protein complex. Thus, sister chromatids are not coaligned along the entire chromosome arm during interphase. The HPC assay allows identification of homologous sequences that are closely juxtaposed during interphase in an unbiased way.

Mechanism and Function of Sister Chromatid Cohesion

The cohesin multi-subunit protein complex mediates sister chromatid cohesion from replication until onset of anaphase. Cohesin core subunits form a tripartite ring around sister chromatids facilitating their tension-generating bi-orientation on the mitotic spindle. Cohesin associates with chromatin prior to replication initiation, yet it becomes cohesive only during replication, via the Eco1 acetyl-transferase. Programmed proteolysis of the cohesin subunit kleisin via a site-specific protease (separase) triggers chromatid separation towards opposite spindle poles at the metaphase-to-anaphase transition. Bulk cohesin dissociates from yeast chromosomes at this transition. In mammals, however, cohesin unloading occurs in several steps, during S-phase, prophase (coinciding with cytologically visible resolution of individualized sister chromatids) and metaphase. A subset of cohesin further remains associated with chromosomes even in telophase.

In yeast, the distribution of cohesin along chromosomes is surprisingly dynamic. Following its loading during G1, at condensin-loading positions, cohesin is shifted to intergenic sites as a consequence of convergent transcription. Genome-wide loading and activation of cohesin further occurs in response to DSB damage during G2, suggesting that intersister connections become reinforced to facilitate DNA repair. In mammals, cohesin stably associates with a distinct sequence motif also occupied by CTCF, a boundary-element protein that controls transcription via its enhancer blocking function.

The dynamic localization pattern of cohesin and its roles in diverse cellular processes may lead to a question of which subset of cohesin actually mediates sister chromatid pairing. This question can be addressed by the Homologous Pairing Capture assay described herein. First, the approach described herein can be used to measure pairing levels at cohesin binding sites. Thus, the approach will identify cohesin subclasses involved in pairing versus those involved in other functions. Second, the assay described herein will assess cohesin-independent pairing in a genome-wide manner. Importantly, select genome regions, including rDNA and telomeres in telomerase deficient cells exhibit delayed mitotic segregation and are linked via cohesin-independent mechanisms. Further, topoisomerase II is required for faithful sister segregation and may play a role in controlling a subset of pairing sites. By assaying pairing at different cell cycle stages and under appropriate mutant conditions the current invention allows to identify subsets of pairing sites potentially controlled by different mechanisms.

Homologous Pairing During Meiosis

Steps and Mechanism

The approach described herein can be used to identify specialized meiotic pairing sites. Such sites would have eluded cytological analysis utilizing arbitrarily chosen FISH signals. Identification of meiotic pairing sequences will make possible to establish determinants of interhomolog pairing. In contrast to sister chromatid cohesion which arises between (tethered) replicated DNA molecules, meiotic pairing between homologous chromosomes occurs de novo. Note that homologs occupy different nuclear territories in most organisms. Homologous pairing is a precondition for all ensuing meiotic chromosomal events, including homolog juxtaposition via the synaptonemal complex (SC), recombination, and reductional chromosome segregation. Cytological studies suggest that homologs become coaligned at the lepotene-zygotene transition, prior to maximum chromosome condensation.

Figure 9:
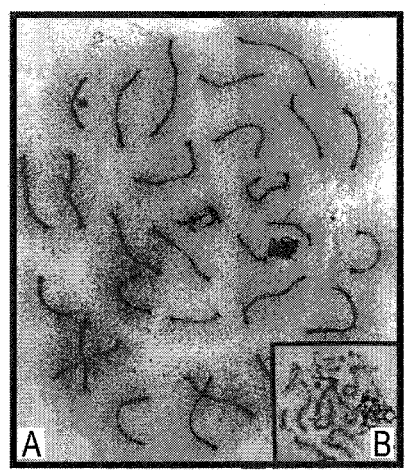
FIG. 9 illustrates pachytene nuclei from moth (A) and yeast (B) shown at identical magnifications. Hypotonically de-condensed chromatin loops emerge from the central synaptonemal complex.

Whether meiotic pairing is established via interactions between designated pairing sites (as for example in *C. elegans*), via a stochastic, protein-mediated process, or via pairing-prone DNA sequences is currently unclear. Following SC assembly, homolog axes are closely juxtaposed along a central proteinaceous central element, with the majority of chromatin organized as loops emerging to both sides. Loop sizes vary among species, between 20 and 2,500 kb depending on genome size, see FIG. 9A and FIG. 9B. The number of loops per micron of SC, however, is approximately constant between species, indicating conserved building principles that dictate loop positions along meiotic homolog pairs. The binding sites of proteins that cytologically localize to the base of chromatin loops, for example meiosis-specific cohesin Rec8, widely overlap with mitotic cohesin binding sites, yet the identity of sequences involved in pairing are unknown.

Factors that mediate meiotic homologous pairing are currently unknown. Proteins with established functions in homology search and/or strand invasion including Rad51 and its meiotic paralog Dmc1 are not required for global meiotic pairing. Meiotic pairing in yeast is stabilized by several recombination steps, including programmed DSB formation and strand invasion. Specific information on preferred paring sequences will allow reevaluating such determinants on a molecular level at natural pairing sites.

Many other benefits will no doubt become apparent from future application and development of this technology.

It will be understood that any one or more feature or component of one embodiment described herein can be combined with one or more other features or components of another embodiment. Thus, the present invention includes any and all combinations of components or features of the embodiments described herein.

All patents, published applications, and articles noted herein are hereby incorporated by reference in their entirety.

As described herein, the present invention solves many problems associated with previously known strategies. However, it will be appreciated that various changes in the details, materials and arrangements of steps, which have been herein described and illustrated in order to explain the nature of the invention, may be made by those skilled in the art without departing from the principle and scope of the invention, as expressed in the appended claims.

What is claimed is:

1. A method for detecting pairing between homologous nucleic acid (DNA) sequences comprising:
    providing a system containing DNA species;
    forming inverted repeats from homologous pairing partners in a portion of the DNA species that include a homologous sequence that is spatially juxtaposed with another homologous sequence wherein forming inverted repeats from homologous pairing partners is performed by generating head-to-head ligation products, whereby the DNA species not including juxtaposed homologous sequences are not converted into inverted repeats;
    forming hairpin DNA molecules from the inverted repeats by rapid intrastrand annealing;
    forming single stranded DNA molecules from another portion of the DNA species that do not contain inverted repeats;
    separating the single stranded DNA molecules from the hairpin DNA molecules, thereby enabling detection of pairing between homologous DNA sequences; wherein rapid intrastrand annealing is performed by denaturation followed by renaturation, and denaturation and renaturation are carried out under conditions that (i) promote intramolecular annealing over intermolecular annealing, and that (ii) allow annealing between homologous sequences but discourage annealing between non-homologous sequences.

2. The method of claim 1 wherein the head-to-head ligation products are formed by DNA fragmentation, followed by ligation of crosslink-connected sequence pairs.

3. The method of claim 2 wherein DNA fragmentation is performed by a process selected from the group consisting of (i) using a restriction enzyme, (ii) sonication, (iii) adaptive focused acoustics, (iv) enzymatic, sequence non-specific fragmentation, and (v) combinations thereof.

4. The method of claim 1 further comprising:
    prior to forming inverted repeats, stabilizing transient pairing interactions.

5. The method of claim 4 wherein stabilizing transient pairing interactions is performed by exposing the DNA species to one or more crosslinking agents to stabilize pairing interactions.

6. The method of claim 5 wherein the crosslinking agent is selected from the group consisting of formaldehyde, dimethyl adipimidate, disuccinimidyl suberate, dithiobis succinimidyl propionate, ethylene glycolbis[succinimidyl succinate], DNA intercalating agents linked to biotinstreptavidin, psoralen, and difunctional alkylating agents.

7. The method of claim 4 wherein stabilizing transient pairing interactions is performed by extraction methods that prevent branch migration.

8. The method of claim 1 wherein the separating step is performed by eliminating single stranded DNA molecules by reaction with a single strand specific nuclease.

9. The method of claim 8 wherein the nuclease is selected from the group consisting of S1 nuclease, P1 nuclease, Mung Bean nuclease, and Exonuclease I.

10. The method of claim 1 wherein the separating step is performed by eliminating single stranded DNA molecules by adsorption of the hairpin DNA molecules to a positively charged resin.

11. The method of claim 10 wherein the positively charged resin is benzoylated naphtholyated diethylaminoethyl cellulose.

12. The method of claim 1 further comprising:
    prior to forming the hairpin DNA molecules, subjecting supercoiled, circular and relaxed, circular DNA in the DNA species to nicking.

13. The method of claim 12 wherein nicking is performed by reacting the circular DNA with an agent selected from the group consisting of a nicking sequence-specific endonuclease, a topoisomerase, and mutant Vvn endonuclease.

14. The method of claim 1 further comprising:
    prior to forming the hairpin DNA molecules, separating supercoiled, circular and relaxed, circular DNA in the DNA species from linear ligation products via 2-dimensional gel electrophoresis.

15. The method of claim 1 further comprising:
    after separating the single stranded DNA molecules from the hairpin DNA molecules, amplifying the remaining hairpin DNA molecules.

16. The method of claim 15 wherein amplifying is performed by a technique selected from the group consisting of linker-mediated polymerase chain reaction and ligation-mediated amplification.

17. The method of claim 1 wherein forming inverted repeats from homologous pairing partners is performed by generating head-to-head ligation products comprising homologous DNA segments.

18. A method for detecting pairing between homologous nucleic acid (DNA) sequences comprising:
    providing a system containing DNA species;
    forming inverted repeats from homologous pairing partners in a portion of the DNA species that include a homologous sequence that is spatially juxtaposed with another homologous sequence wherein forming inverted repeats from homologous pairing partners is performed by generating head-to-head ligation products, whereby the DNA species not including juxtaposed homologous sequences are not converted into inverted repeats;
    forming hairpin DNA molecules from the inverted repeats by rapid intrastrand annealing;
    forming single stranded DNA molecules from another portion of the DNA species that do not contain inverted repeats;
    separating from linear DNA the supercoiled, circular and relaxed, circular DNA molecules generated as a byproduct of DNA ligation during formation of inverted repeats and separating the single stranded DNA molecules from the hairpin DNA molecules, thereby enabling detection of pairing between homologous DNA sequences; wherein rapid intrastrand annealing is performed by denaturation followed by renaturation, and denaturation and renaturation are carried out under conditions that (i) promote intramolecular annealing over intermolecular annealing, and that (ii) allow annealing between homologous sequences but discourage annealing between non-homologous sequences.

* * * * *